United States Patent [19]
Kato et al.

[11] Patent Number: 5,935,101
[45] Date of Patent: Aug. 10, 1999

[54] TWO-COMPARTMENT TYPE PREFILLED SYRINGE

[75] Inventors: Masahiko Kato, Amagasaki; Nobuo Tanaka, Mishima-gun; Muneo Nonomura, Toyonaka; Makoto Kakiuti, Takahagi, all of Japan

[73] Assignee: Takeda Chemical Industries, Ltd., Osaka, Japan

[21] Appl. No.: 09/006,862

[22] Filed: Jan. 14, 1998

[30] Foreign Application Priority Data

Jan. 30, 1997 [JP] Japan .................................. P9-031160

[51] Int. Cl.$^6$ .................................................. A61M 37/00
[52] U.S. Cl. ................. 604/82; 604/89; 604/90; 604/181; 604/187; 604/232
[58] Field of Search .................. 604/82, 89, 90, 604/91, 181, 187, 191, 214, 232, 236, 238

[56] References Cited

U.S. PATENT DOCUMENTS

4,792,329 12/1988 Schreuder .................................. 604/90

*Primary Examiner*—Wynn Wood Coggins
*Assistant Examiner*—N. Kent Gring
*Attorney, Agent, or Firm*—Wenderoth, Lind & Ponack, L.L.P.

[57] ABSTRACT

A two-compartment type prefilled syringe includes a first rubber stopper fitted into a front sleeve, a second rubber stopper fitted into a rear end portion of a cartridge, a third rubber stopper for hermetically dividing the interior of the cartridge into front and rear compartments and a bypass formed by radially outwardly bulging a portion of a peripheral wall of the cartridge. In an axial direction of the cartridge, a length of the third rubber stopper is slightly smaller than an inner length of the bypass. When the third rubber stopper has been displaced into the bypass, the sealing property of the rear compartment with the front compartment is cancelled such that the dissolving agent, suspension or the like in the rear compartment is carried, via the bypass, into the front compartment containing dry medicament or the like. A ratio of a maximum width of one end of the bypass adjacent to the front sleeve to a maximum width of the other end of the bypass adjacent to the rear end portion of the cartridge is set to range from 1.2 to 5.0.

9 Claims, 5 Drawing Sheets

TWO-COMPARTMENT TYPE PREFILLED SYRINGE

BACKGROUND OF THE INVENTION

The present invention generally relates to a two-compartment type prefilled syringe in which the interior of a cartridge made of glass or plastic is divided into front and rear compartments by a plurality of rubber stoppers, and more particularly and to improvement of a bypass for communicating the front and rear compartments with each other which is formed by bulging a peripheral wall of the cartridge radially outwardly.

Figure 6:
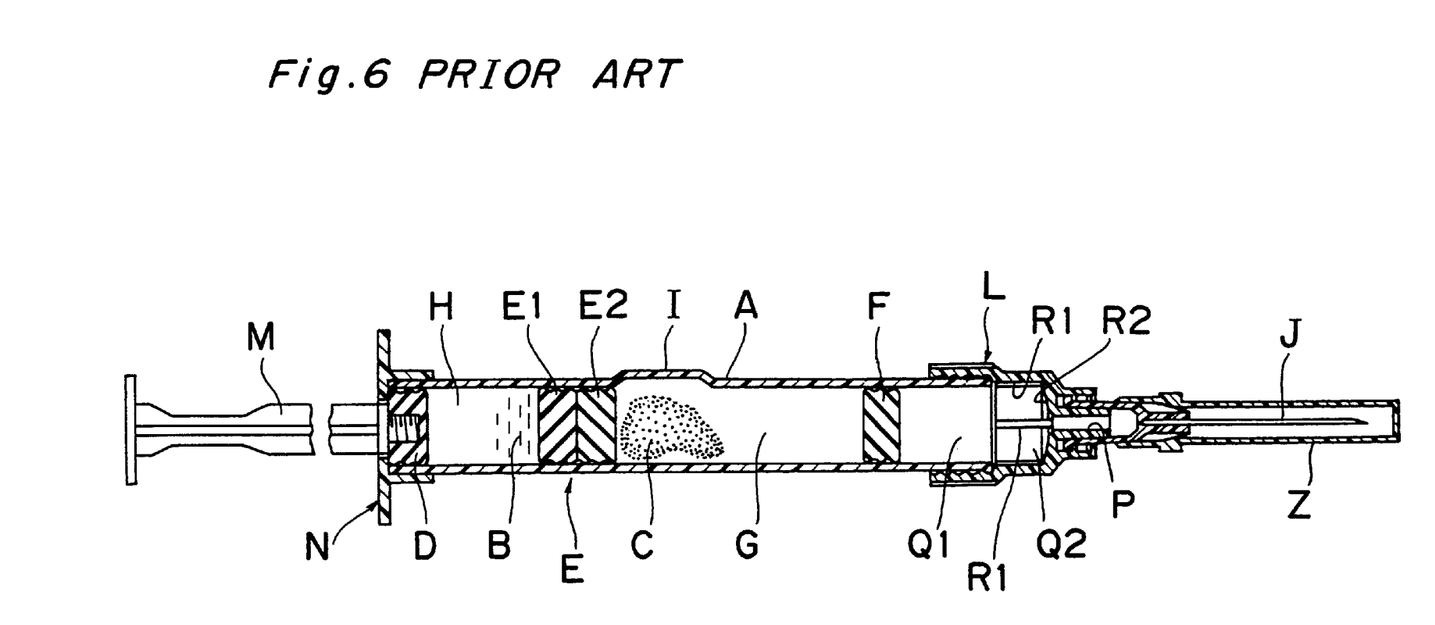
FIG. 6 is a schematic sectional view of a prior art two-compartment type prefilled syringe.

A two-compartment type prefilled syringe having such a construction is known from, for example, Japanese Patent Laid-Open Publication No. 62-5357 (1987) and Japanese Utility Model Publication No. 3-31302 (1991). In the known two-compartment type prefilled syringe disclosed in the former document, a first rubber stopper F disposed adjacent to a front sleeve L, a second rubber stopper D disposed adjacent to a finger grip N acting as an inlet for a plunger rod M and a third rubber stopper E disposed between the first and second rubber stoppers F and D are provided in a cartridge A made of glass or plastic as shown in FIG. 6. The interior of the cartridge A is hermetically divided into a front compartment C and a rear compartment B by the third rubber stopper E. The third rubber stopper E is constituted by a rear third rubber stopper E1 and a front third rubber stopper E2.

A bypass I for communicating the front and rear compartments C and B with each other is formed by radially outwardly bulging a portion of a peripheral wall of the cartridge A disposed between the first rubber stopper F and the third rubber stopper E.

In the known two-compartment type prefilled syringe having the construction shown in FIG. 6, the first rubber stopper F is displaced to a front end chamber Q2 through a front chamber Q1 at an initial stage of depression of the plunger rod M. By grooves R1 and R2 formed on an inner surface of a peripheral wall of the front end chamber Q2, the front chamber Q1 and the front end chamber Q2 are communicated with a bore P leading to an injection needle J. When the plunger rod M is further depressed, the second rubber stopper D is advanced, and thus the third rubber stopper E is pushed towards the front compartment C by the internal pressure of pharmaceutical liquid, such as dissolving agent H filled in the rear compartment B in liquid-tight condition.

At the moment the third rubber stopper E has been displaced into the bypass I, the rear compartment B and the front compartment C are communicated with each other by a gap between the bypass I and the third rubber stopper E, so that the pharmaceutical liquid, such as the dissolving agent H, of the rear compartment H flows into the front compartment C at a high velocity so as to suspend or dissolve dry medicament G. At an initial stage of communication between the rear compartment B and the front compartment C, the pharmaceutical liquid such as the dissolving agent H, which has passed through the bypass I, has high kinetic energy and thus, impinges like a squirt upon a rear face of the first rubber stopper F in the front end chamber Q2. As a result, the pharmaceutical liquid such as the dissolving agent H flows into the grooves R1 and R2 of the front end chamber Q2 while suspend the dry medicament G sufficiently or reaching the injection needle J from the bore P without dissolving the dry medicament G.

Meanwhile, the front third rubber stopper E2 is fitted into the cartridge A from the front chamber Q1 for the purpose of sealing the rear compartment B and the front compartment C in liquid-tight condition and preventing transfer of moisture to the dry medicament G of the front compartment C from the rear third rubber stopper E1 which has absorbed moisture by steam sterilization performed after pour and sealing of the pharmaceutical liquid such as the dissolving agent H.

Figure 7:
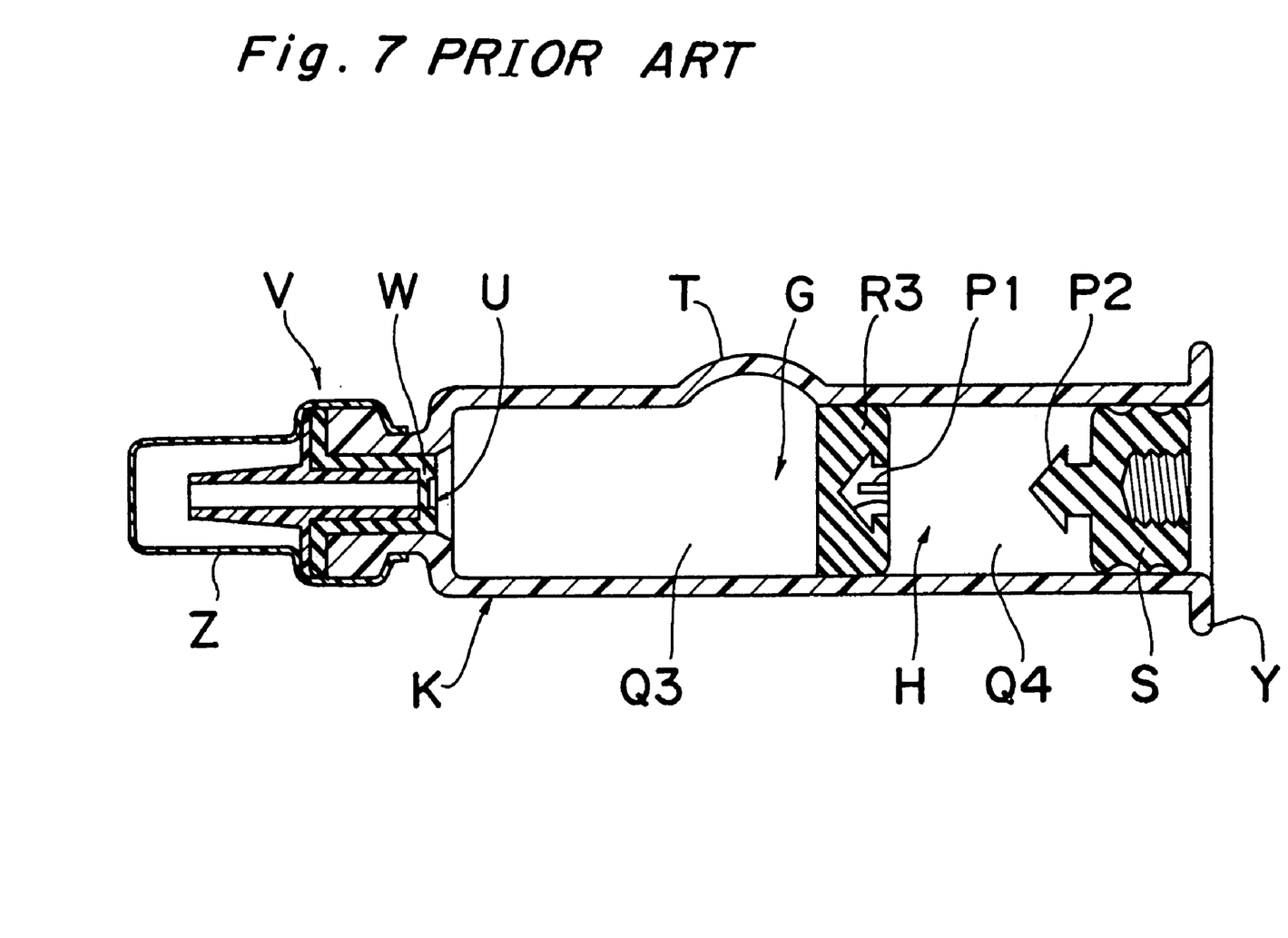
FIG. 7 is a schematic sectional view of a further prior art two-compartment type prefilled syringe.

On the other hand, in the conventional two-compartment type prefilled syringe disclosed in the latter document, a gasket S disposed adjacent to a finger grip Y confronting a plunger rod (not shown) is fitted into a peripheral wall of a cartridge K, while a first rubber stopper W is fitted into a front sleeve V as shown in FIG. 7. Furthermore, a third rubber stopper R3 is fitted inside the peripheral wall of the cartridge K so as to be disposed between the gasket S and the first rubber stopper W. The interior of the cartridge K is divided into a front compartment Q3 and a rear compartment Q4 by the third rubber stopper R3. The dry medicament G is filled in the front compartment Q3, while the dissolving liquid H is filled in the rear compartment Q4. A bypass T for communicating the front compartment Q3 and the rear compartment Q4 with each other is formed by radially outwardly bulging a portion of the peripheral wall of the cartridge K disposed between the first rubber stopper W and the third rubber stopper R3. A concave engageable portion P1 and a convex engageable portion P2 are, respectively, formed on a rear face of the third rubber stopper R3 and a front face of the second rubber stopper S so as to confront each other. When the rear face of the third rubber stopper R3 and the front face of the second rubber stopper S have been brought into contact with each other, the convex engageable portion P2 of the second rubber stopper S is brought into engagement with the concave engageable portion P1 of the third rubber stopper R3 so as to integrally couple the second and third rubber stoppers S and R3 with each other.

Prior to use of the conventional two-compartment type prefilled syringe of FIG. 7, a double-pointed needle (not shown) is mounted on the front sleeve V so as to pierce the first rubber stopper W. Subsequently, when the second rubber stopper S is advanced by the plunger rod screwed into a threaded portion of the second rubber stopper S, the internal pressure of the dissolving agent H of the rear compartment Q4 rises, so that the third rubber stopper R3 is advanced into the bypass T. At the moment the rear compartment Q4 and the front-compartment Q3 have been communicated with each other, the dissolving agent H, having high kinetic energy, is drawn into the front compartment Q3 like a squirt so as to reach the first rubber stopper W.

At the time the whole amount of the dissolving agent H in the rear compartment Q4 has displaced to the front compartment Q3, the second rubber stopper S is brought into contact with the third rubber stopper R3. Therefore, the convex engageable portion P2 of the second rubber stopper S is brought into engagement with the concave engageable portion P1 of the third rubber stopper R3 so as to couple the second and third rubber stoppers S and R3 with each other integrally.

In both of the prior art two-compartment type prefilled syringes of FIGS. 6 and 7, an operation for delivering the pharmaceutical liquid such as the dissolving agent in the rear compartment to the front compartment containing the dry medicament is performed in a state in which the injection needle is fitted into the syringe. Therefore, a drawback happen in that since only the pharmaceutical liquid leaks out of the injection needle prior to suspension or dissolution of the dry medicament due to the above mentioned squirt phenomenon of the pharmaceutical liquid such as the dissolving agent, the amount of the dissolving agent is less than that required for dissolving the dry medicament in the front compartment, thereby resulting in improper dissolution of the dry medicament.

In order to prevent the above mentioned squirt phenomenon of the pharmaceutical liquid, an operator has to adjust the depression of the plunger rod in a sophisticated manner, thus resulting in the disadvantage that it is extremely difficult to operate the syringe.

Furthermore, the only measure for preventing the squirt phenomenon in the constructions of the prior art two-compartment type prefilled syringes is to increase the volume of the front compartment to an unnecessary degree. Therefore, there has been a demand for a means for preventing the squirt phenomenon without incurring An increase in the volume of the front compartment.

In addition, it is not preferable that prior to injection, the dissolving agent adheres to an outer side of the injection needle and an inner side of a cap Z (FIG. 6) due to the squirt phenomenon.

SUMMARY OF THE INVENTION

Accordingly, an essential object of the present invention is to provide, with a view to eliminating the above mentioned disadvantages of prior art two-compartment type prefilled syringes, a two-compartment type prefilled syringe in which a size of one end of a bypass adjacent to a rear end portion of a cartridge is minimized and a size of the other end of the bypass adjacent to a front end portion of the cartridge, i.e., a size of a path leading to a front compartment, is increased so as to maximize an area of a gap defined by the other end of the bypass and a third rubber stopper. The vigor of the dissolving agent carried into the bypass by pressure in a rear compartment upon depression of a plunger rod is greatly diminished the by increase of area of the bypass so as to cause the dissolving agent to flow slowly not only is the risk that the dissolving agent is drawn into an injection needle together with air in the front compartment due to squirting eliminated, but the required amount of the dissolving agent is slowly carried into the front compartment by minimizing the amount of the dissolving agent left in the bypass after the administration of the injection liquid.

In order to accomplish this object of the present invention, a two-compartment type prefilled syringe according to the present invention comprises a cartridge, a front sleeve which is mounted on a front end portion of the cartridge and has an injection needle mounted thereon, and a first rubber stopper which is fitted into an front sleeve and is pierced through by the injection needle prior to use of the prefilled syringe. A second rubber stopper is fitted into a rear end portion of the cartridge. A plunger rod is attached to the second rubber stopper. A third rubber stopper which is fitted into the cartridge so as to be disposed between the first rubber stopper and the second rubber stopper such that the interior of the cartridge is hermetically divided into a front compartment defined between the first rubber stopper and the third rubber stopper and a rear compartment defined between the third rubber stopper and the second rubber stopper. A bypass is formed by radially outwardly bulging a portion of a peripheral wall of the cartridge disposed between the first rubber stopper and the third rubber stopper. In an axial direction of the cartridge, a length of the third rubber stopper is slightly smaller than an inner length of the bypass. When the third rubber stopper has been displaced into the bypass, the sealing property of the rear compartment against the front compartment is cancelled such that dissolving agent, suspension or the like in the rear compartment is carried, via the bypass, into the front compartment containing dry medicament or the like. A ratio of a maximum width of one end of the bypass adjacent to the front sleeve to a maximum width of the other end of the bypass adjacent to the rear end portion of the cartridge is set in a range from 1.2 to 5.0.

BRIEF DESCRIPTION OF THE DRAWINGS

The above object and features of the present invention will become apparent from the following description taken in conjunction with the preferred embodiments thereof with reference to the accompanying drawings, in which.

Before the description of the present invention proceeds, it is to be noted that like parts are designated by like reference numerals throughout the several views of the accompanying drawings.

DETAILED DESCRIPTION OF THE INVENTION

Figure 1:
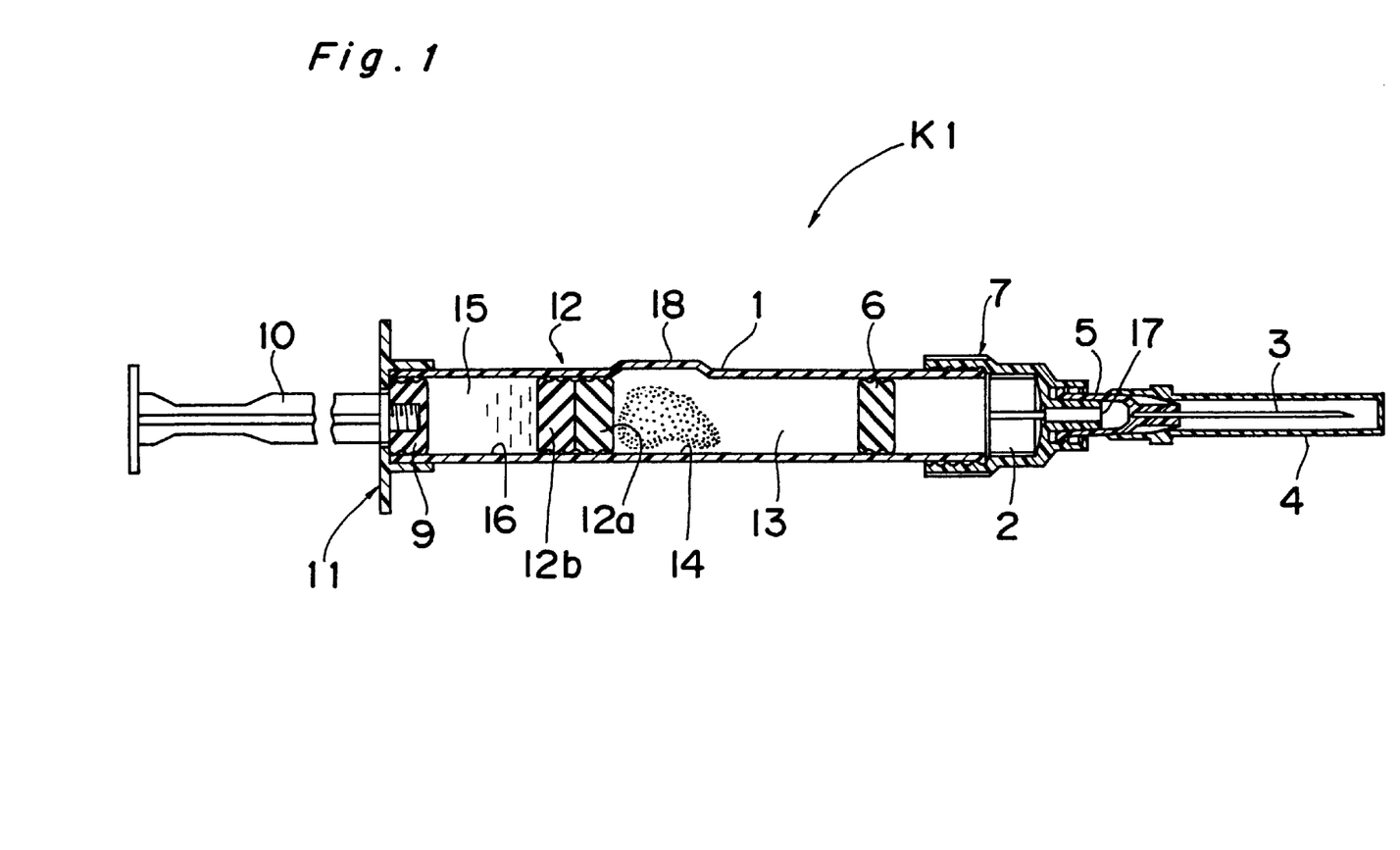
FIG. 1 is a sectional view of a two-compartment type prefilled syringe according to a first embodiment of the present invention.

FIG. 1 shows a two-compartment type prefilled syringe K1 according to a first embodiment of the present invention. A bypass 18 of the prefilled syringe K1 is structurally identical with that of a prior art two-compartment type prefilled syringe of FIG. 6. A front sleeve 7 has an inside diameter slightly larger than an outside diameter of a cartridge 1 and is fitted around a front open end 2 of the cartridge 1. A needle base 5 provided with a cap 4 for protecting an injection needle 3 is mounted on a distal end 17 of the front sleeve 7 such that the needle base 5 is communicated with the front sleeve 7 at the distal end 17.

A first rubber stopper 6 is fitted into a peripheral wall of the cartridge 1 in liquid-tight condition in the vicinity of the front sleeve 7, while a second rubber stopper 9 is fitted into the peripheral wall of the cartridge 1 in liquid-tight condition at a finger grip 11 acting as an inlet for a plunger rod 10. A third rubber stopper 12 is fitted into the peripheral wall of the cartridge 1 so as to be disposed between the first rubber stopper 6 and the second rubber stopper 9 and includes a front third rubber stopper 12a and a rear third rubber stopper 12b.

The interior of the cartridge 1 is hermetically divided by the third rubber stopper 12 into a front compartment 14 defined between the first rubber stopper 6 and the third rubber stopper 12 and a rear compartment 16 defined between the second rubber stopper 9 and the third rubber stopper 12. Medicament such as dry medicament 13 is filled into the front compartment 14, while pharmaceutical liquid such as dissolving agent 15 and suspension is filled into the rear compartment 16. A bypass 18 is formed by radially outwardly bulging a portion of the peripheral wall of the cartridge 1 disposed between the first rubber stopper 6 and the third rubber stopper 12.

Figure 2:
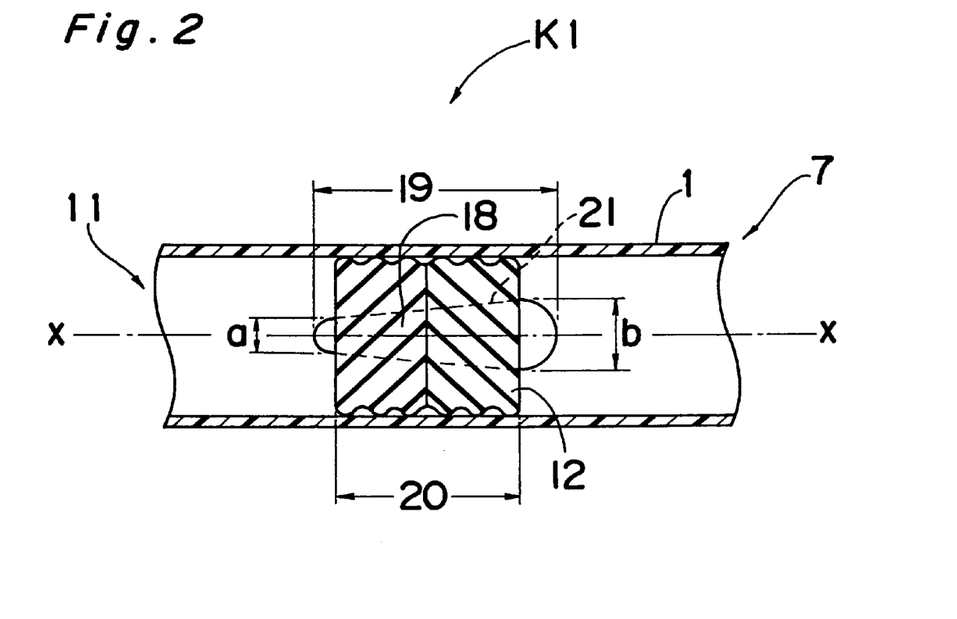
FIG. 2 is a schematic top plan view showing a bypass of the prefilled syringe of FIG. 1.

In an axial direction of the cartridge 1 along the line x—x shown in FIG. 2, a length 19 of the bypass 18 is slightly larger than a length 20 of the third rubber stopper 12 as in prior art. Thus, the when the third rubber stopper 12 has been displaced into the bypass 18, sealing property of the rear compartment 16 is cancelled, and thus the dissolving agent 15 or the suspension in the rear compartment 16 is carried into the front compartment 14 via the bypass 18.

In the present invention, the flow velocity and state of flow of the dissolving agent 15 delivered to the front compartment 14 by way of the bypass 18 are changed according to the shape of the bypass 18. As described below shape of the bypass 18 is selected so as to prevent a phenomenon in which the dissolving agent 15 is discharged out of the injection needle 3 like a squirt. This phenomenon is referred to as a "squirt phenomenon" below.

In FIG. 2 showing the first embodiment, the cartridge 1 is oriented in the same direction as in FIG. 1. Therefore, the bypass 18 has a maximum width a at its one end adjacent to the finger grip 11 and a maximum width b at the other end adjacent to the front sleeve 7. A ratio of the maximum width b to the maximum width a is set to range from 1.2 to 5.0. Meanwhile, in the axial direction of the cartridge 1 along the line x—x in FIG. 2, the length 19 of the bypass 18 is set to be slightly larger than the length 20 of the third rubber stopper 12. Opposite side edges 21 of the bypass 18 connecting the opposite ends of the bypass 18 are formed rectilinearly.

In order to determine the maximum widths a and b of the opposite ends of the bypass 18 and the length 19 of the bypass 18 and the length 20 of the third rubber stopper 12 in the axial direction of the cartridge 1 along the line x—x in FIG. 2 as described above, the following experiments 1 to 7 were conducted so as to determine the proper range of ratio R of the maximum width b to the maximum width a by observing the flow of the dissolving agent 15 to the front compartment 14 via the bypass 18 at the time of depression of the plunger rod 10.

In the experiments, the maximum width a of the one end of the bypass 18 adjacent to the finger grip 11 was set at 2.0 mm and 5.0 mm and state of the dissolving agent 15 flowing into the front compartment 14 through the bypass 18 was observed by changing the maximum width b of the other end of the bypass 18 adjacent to the front sleeve 7. The experiments were aimed at minimizing the maximum width a of the one end of the bypass 18, eliminating the squirt phenomenon and minimizing the amount of the dissolving agent 15 left in the bypass 18 after the administration of injection liquid. Each experiment was conducted 10 times under the following conditions (i) to (iii).

(i) The cartridge 1 is made of glass subjected to silicone treatment and has an inside diameter of 14 mm.

(ii) The third rubber stopper 12 has a total width of 12 mm.

(iii) The plunger rod 10 is depressed at a speed of 15 cm/min.

Meanwhile, experimental results were classified into four ranks in an ascending order of preference, i.e., a rank D in which there is a strong possibility of leakage of the dissolving agent 15 from the injection needle 3 directly or through guide grooves of the cartridge 1, in which the dissolving agent 15 having passed through the bypass 18 impinges upon a rear face of the first rubber stopper 6 or a bottom of the front sleeve 7 vigorously in a stream, a rank C in which there is a possibility of leakage of the dissolving agent 15 from the injection needle 3, in which the dissolving agent 15 flows into the front compartment 14 in a stream but feebly, a rank B in which there is little possibility of leakage of the dissolving agent 15 from the injection needle 3, in which the dissolving agent 15 flows into the front compartment 14 at a low velocity, and a rank A in which there is no possibility of leakage of the dissolving agent 15 from the injection needle 3, in which the dissolving agent 15 flows into the front compartment 14 at quite a low speed and merely forms a slightly curved stream at an outlet of the bypass 18.

[1] Experiment 1 (a=2.0 mm, b=2.0 mm, R=1.0)
   (1) Rank D: 10
[2] Experiment 2 (a=5.0 mm, b=5.0 mm, R=1.0)
   (1) Rank D: 9
   (2) Rank C: 1
[3] Experiment 3 (a=2.0 mm, b=2.4 mm, R=1.2)
   (1) Rank B: 8
   (2) Rank A: 2
[4] Experiment 4 (a=2.0 mm, b=4.0 mm, R=2.0)
   (1) Rank B: 5
   (2) Rank A: 5
[5] Experiment 5 (a=2.0 mm, b=8.0 mm, R=4.0)
   (1) Rank B: 3
   (2) Rank A: 7
[6] Experiment 6 (a=2.0 mm, b=10.0 mm, R=5.0)
   (1) Rank A: 10
[7] Experiment 7 (a=2.0 mm, b=12.0 mm, R=6.0)
   (1) Rank A: 10

In the above experiments 1 to 7, as the value b becomes larger, amount of the dissolving agent 15 left in the bypass 18 after administration of the injection liquid also increases. Thus, especially in case the ratio R is 6.0 as in the experiment 7, the squirt phenomenon can be eliminated, but the amount of the dissolving agent 15 left in the bypass 18 after administration of the injection liquid is large, which is unsuitable for practical use.

From the above results, it is understood that when a narrow gap of the bypass 18 is widened, namely, the cross-sectional area of the bypass 18 is increased by a gradual increase of the width of a flow path from the maximum width a to the maximum width b of the bypass 18 at the time the dissolving agent 15 flows into the front compartment 14 via the bypass 18 upon depression of the plunger rod 10, the flow velocity of a predetermined amount of the dissolving agent 15 delivered upon depression of the plunger rod 10 is reduced, and thus the dissolving agent 15 flows into the front compartment 14 slowly. It was confirmed in this case that the squirt phenomenon does not happen in which the dissolving agent 15, initially having passed through the bypass 18, flows through the front compartment 14 without dissolving the dry medicament 13, such as powdery medicament, in the front compartment 14 and then leaks out of the injection needle 3 together with air in the front compartment 14.

Figure 3:
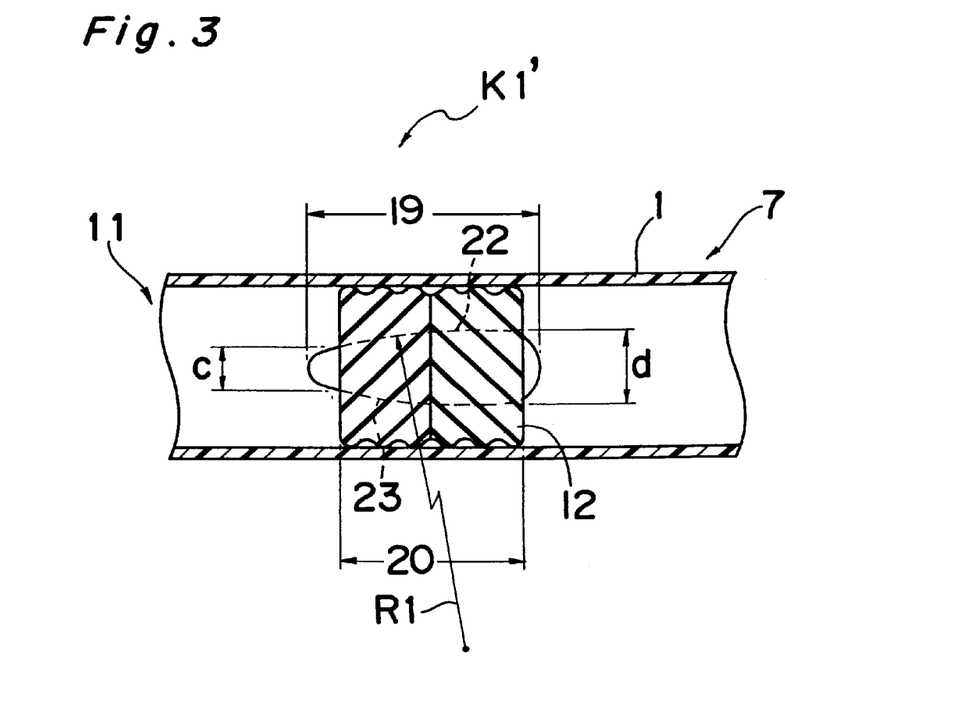
FIG. 3 is a view similar to FIG. 2, particularly showing a first modification.

FIG. 3 shows a two-compartment type prefilled syringe K1' which is a first modification of the prefilled syringe K1. The prefilled syringe K1' includes a bypass 22. The bypass 22 has a maximum width c at its one end adjacent to the finger grip 11 and a maximum width d at the other end adjacent to the front sleeve 7. Opposite side edges 23 of the bypass 22 connecting the opposite ends of the bypass 22 are each formed by a gentle convex arc having a large radius R1.

In the prefilled syringe K1', a ratio of the maximum width d to the maximum width c is set to range from 1.2 to 5.0 and the length 19 of the bypass 22 is set to be slightly larger than the length 20 of the third rubber stopper 12 in the axial direction of the cartridge 1 in the same manner as the prefilled syringe K1.

Therefore, in the prefilled syringe K1', when the dissolving agent 15 flows into the front compartment 14 through the bypass 22, the flow velocity of the dissolving agent 15 is reduced by increase of width of a flow path from the maximum width c to the maximum the width d of the bypass 22. Each of the opposite side edges 23 of the bypass 22 is formed by the gentle arc having the large radius R1 so as to change the cross-sectional area of the bypass 22 taken along a line orthogonal to the axial direction of the cartridge 1, more than the rectilinear side edges 21 of the bypass 18 of the prefilled syringe K1. The dissolving agent 15 flows through the bypass 22 slightly turbulently as compared with the rectilinear side edges 21 of the bypass 18 of the prefilled syringe K1, so that the flow velocity of the dissolving agent 15 is further reduced from the prefilled syringe K1, and thus the dissolving agent 15 flows into the front compartment 14 rather slowly.

Figure 4:
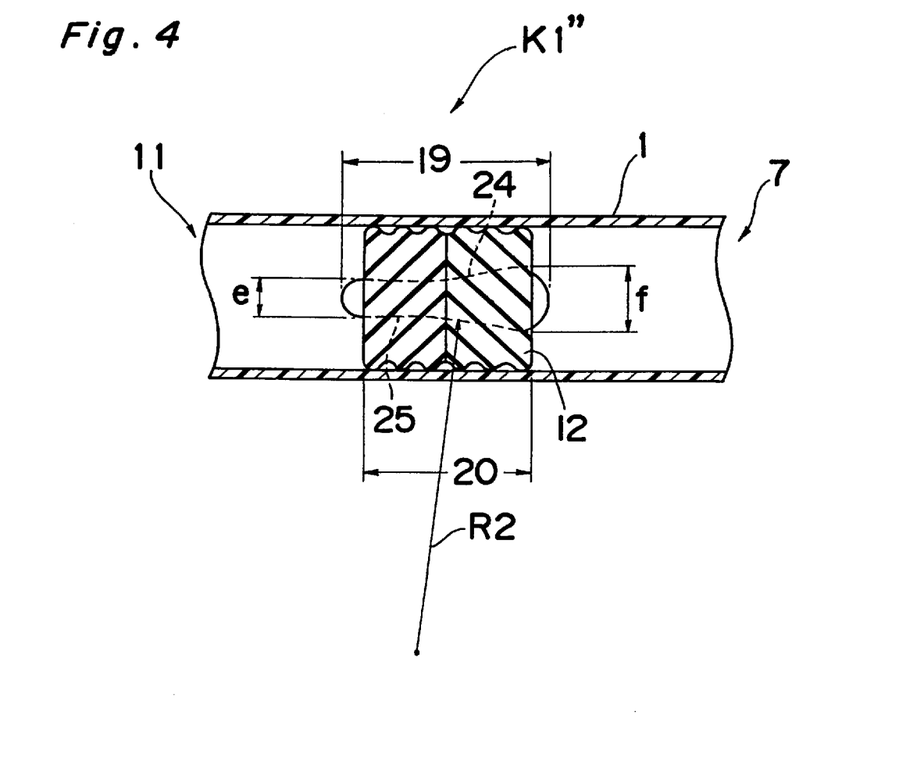
FIG. 4 is a view similar to FIG. 2, particularly showing a second modification.

FIG. 4 shows a two-compartment type prefilled syringe K1" which is a second modification of the prefilled syringe K1. The prefilled syringe K1" includes a bypass 24. The bypass 24 has a maximum width e at its one end adjacent to the finger grip 11 and a maximum width f at the other end adjacent to the front sleeve 7. Opposite side edges 25 of the bypass 24 connecting the opposite ends of the bypass 24 are each formed by a gentle concave arc having a large radius R2 such that the bypass 24 has a gourdlike shape. However, even if the other end of the bypass 24 adjacent to the front sleeve 7 is formed into a mushroomlike shape, similar effects can be gained.

When the dissolving agent 15 passes through the bypass 24, the flow of the dissolving agent 15 is made slightly turbulent by the change of the cross section of the flow path of the bypass 24 due to the gently concave side edges 25 of the bypass 24, and thus, the flow velocity of the dissolving agent 15 is further reduced also by increase of the ratio of the maximum width f to the maximum width e of the bypass 24.

In the prefilled syringes K1 to K1", the flow velocity of the dissolving agent 15 is reduced not only by an increase from the width of the one end of the bypass to that of the other end of the bypass but by a change of the cross section of the flow path of the bypass due to the shape and bulging of the opposite side edges of the bypass.

Figure 5:
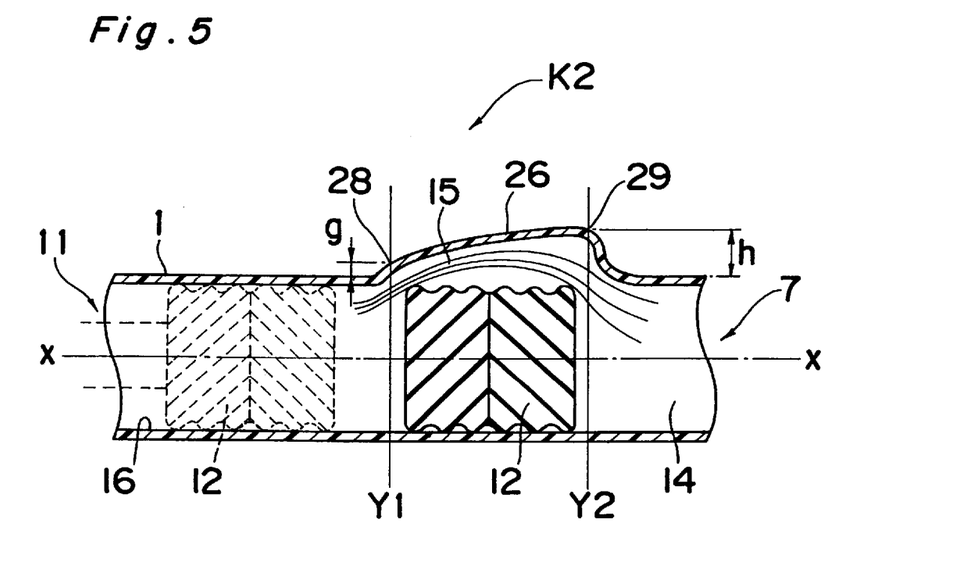
FIG. 5 is a schematic sectional view of a bypass of a two-compartment type prefilled syringe according to a second embodiment of the present invention.

FIG. 5 shows a two-compartment type prefilled syringe K2 according to a second embodiment of the present invention. The prefilled syringe K2 includes a bypass 26. The bypass 26 has one wall end 28 adjacent to the finger grip 11 and the other wall end 29 adjacent to the front sleeve 7. In the bypass 26, the peripheral wall of the cartridge 1 is bulged gradually radially outwardly further from the one end 28 towards the other end 29 such that a ratio of a cross-sectional area of the bypass 26 taken along a plane Y2 orthogonal to the axial direction of the cartridge 1 at the other wall end 29 to that taken along a plane Y1 orthogonal to the axial direction of the cartridge 1 at the one wall end 28 ranges from 1.2 to 5.0 approximately. Since other constructions of the prefilled syringe K2 are similar to those of the prefilled syringe K1, the description is abbreviated.

When the plunger rod 10 is depressed in the prefilled syringe K2, the third rubber stopper 12 is displaced forwardly towards the front sleeve 7 from the position shown by the broken line and occupies the position shown by the solid line as shown in FIG. 5. At this time, the sealing property of the third rubber stopper 12 against the rear compartment 16 is cancelled, so that the dissolving agent 15 filled in the rear compartment 16 flows into the front compartment 14 via the bypass 26. Since the flow rate of the dissolving agent 15 obtained by depression of the plunger rod 10 at this time is considered to be constant, the flow velocity of the dissolving agent 15 is inversely proportional to the cross-sectional area of the bypass 26. Therefore, the flow velocity of the dissolving agent 15 is reduced at a ratio of 1.2 to 5.0 from the one wall end 28 to the other wall end 29 of the bypass 26. As will be seen from the streamline of the dissolving agent 15 shown in FIG. 5, the dissolving agent 15 is diffused more at the other wall end 29 of the bypass 26 than at the one wall end 28 of the bypass 26. The flow velocity of the dissolving agent 15 is reduced from the one wall end 28 of the bypass 26 towards the other wall end 29 of the bypass 26 so that it is possible to prevent the squirt phenomenon in which the dissolving agent 15 is spouted into the front compartment 14 like a squirt.

The one wall end 28 of the bypass 26 is projected radially outwardly through a distance g from the peripheral wall of the cartridge 1, while the other wall end 29 of the bypass 26 is projected radially outwardly through a distance h from the peripheral wall of the cartridge 1. If a difference between the distance h and the distance g, i.e., (h~g) is selected in accordance with an interval between the planes Y1 and Y2, degree of change of flow velocity of the dissolving agent 15 can be set easily.

In the present invention, the bypass formed by radially outwardly bulging the portion of the peripheral wall of the cartridge disposed between the first rubber stopper and the third rubber stopper is shaped such that not only the dimension of the one end of the bypass adjacent to the finger grip is minimized, but the dimension of the other end of the bypass adjacent to the front sleeve is increased.

Therefore, in accordance with the present invention, since the vigor of the dissolving agent is diminished greatly by a slight increase of volume of the bypass, the dissolving agent flows slowly, and thus, the squirt phenomenon can be prevented.

Meanwhile, in accordance with the present invention, it is possible to eliminate the risk of the dissolving agent flows directly into the injection needle together with air in the front compartment.

Furthermore, in accordance with the present invention, since a required amount of the dissolving agent can flow slowly into the medicament in the front compartment, an excellent injection liquid can be obtained and the amount of the dissolving agent left in the prefilled syringe after administration of the injection liquid can be minimized.

What is claimed is:

1. A two-compartment type prefilled syringe comprising:
   a cartridge;
   a front sleeve which is mounted on a front end portion of the cartridge and has an injection needle mounted thereon;
   a first rubber stopper which is fitted into the front sleeve and is pierced through by the injection needle prior to use of the prefilled syringe;
   a second rubber stopper which is fitted into a rear end portion of the cartridge;
   a plunger rod which is attached to the second rubber stopper;

a third rubber stopper which is fitted into the cartridge so as to be disposed between the first rubber stopper and the second rubber stopper such that an interior of the cartridge is hermetically divided into a front compartment defined between the first rubber stopper and the third rubber stopper and a rear compartment defined between the third rubber stopper and the second rubber stopper; and a bypass comprising a radially outwardly bulging portion of a peripheral wall of the cartridge disposed between the first rubber stopper and the third rubber stopper;

wherein in an axial direction of the cartridge, a length of the third rubber stopper is slightly smaller than an inner length of the bypass;

wherein when the third rubber stopper has been displaced into the bypass, a sealing property of the rear compartment with respect to the front compartment is cancelled such that a dissolving agent, suspension or the like in the rear compartment is carried, via the bypass, into the front compartment containing dry medicament or the like; and wherein a ratio of a maximum width of one end of the bypass adjacent to the front sleeve to a maximum width of the other end of the bypass adjacent to the rear end portion of the cartridge is set to range from 1.2 to 5.0.

2. A two-compartment type prefilled syringe comprising:

a cartridge;

a front sleeve which is mounted on a front end portion of the cartridge and has an injection needle mounted thereon;

a first rubber stopper which is fitted into the cartridge in the vicinity of the front sleeve;

a second rubber stopper which is fitted into a rear end portion of the cartridge;

a plunger rod which is attached to the second rubber stopper;

a third rubber stopper which is fitted into the cartridge so as to be disposed between the first rubber stopper and the second rubber stopper such that an interior of the cartridge is hermetically divided into a front compartment defined between the first rubber stopper and the third rubber stopper and a rear compartment defined between the first rubber stopper and the second rubber stopper; and a bypass comprising a radially outwardly bulging portion of a peripheral wall of the cartridge disposed between the first rubber stopper and the third rubber stopper;

wherein in an axial direction of the cartridge, a length of the third rubber stopper is slightly smaller than an inner length of the bypass;

wherein the third rubber stopper has been displaced into the bypass, a sealing property of the rear compartment with respect to the front compartment is cancelled such that a dissolving agent, suspension or the like in the rear compartment is carried, via the bypass, into the front compartment containing a dry medicament or the like;

wherein at an initial stage of depression of the plunger rod, the first rubber stopper is displaced into the front sleeve such that the front compartment and the injection needle are communicated with each other; and wherein a ratio of a maximum width of one end of the bypass adjacent to the front sleeve to a maximum width of the other end of the bypass adjacent to the rear end portion of the cartridge is set to range from 1.2 to 5.0.

3. A two-compartment type prefilled syringe as claimed in claim 1, wherein opposite side edges of the bypass connecting the one end and the other end of the bypass are formed rectilinearly.

4. A two-compartment type prefilled syringe as claimed in claim 2, wherein opposite side edges of the bypass connecting the one end and the other end of the bypass are formed rectilinearly.

5. A two-compartment type prefilled syringe as claimed in claim 1, wherein each of opposite side edges of the bypass connecting the one end and the other end of the bypass is formed by a gentle convex arc.

6. A two-compartment type prefilled syringe as claimed in claim 2, wherein each of opposite side edges of the bypass connecting the one end and the other end of the bypass is formed by a gentle convex arc.

7. A two-compartment type prefilled syringe as claimed in claim 1, wherein each of opposite side edges of the bypass connecting the one end and the other end of the bypass is formed by a gentle concave arc.

8. A two-compartment type prefilled syringe as claimed in claim 2, wherein each of opposite side edges of the bypass connecting the one end and the other end of the bypass is formed by a gentle concave arc.

9. A two-compartment type prefilled syringe comprising:

a cartridge;

a front sleeve which is mounted on a front end portion of the cartridge and has an injection needle mounted thereon;

a first rubber stopper which is fitted into the front sleeve;

a second rubber stopper which is fitted into a rear end portion of the cartridge;

a plunger rod which is attached to the second rubber stopper;

a third rubber stopper which is fitted into the cartridge so as to be disposed between the first rubber stopper and the second rubber stopper such that an interior of the cartridge is hermetically divided into a front compartment defined between the first rubber stopper and the third rubber stopper and a rear compartment defined between the third rubber stopper and the second rubber stopper; and a bypass comprising a radially outwardly bulging portion of a peripheral wall of the cartridge disposed between the first rubber stopper and the third rubber stopper;

wherein in an axial direction of the cartridge, a length of the third rubber stopper is slightly smaller than an inner length of the bypass;

wherein when the third rubber stopper has been displaced into the bypass, a sealing property of the rear compartment is cancelled such that a dissolving agent, suspension or the like in the rear compartment is carried, via the bypass, into the front compartment;

wherein the portion of the peripheral wall of the cartridge rises gradually radially outwardly further from one end of the bypass adjacent to the rear end portion of the cartridge towards the other end of the bypass adjacent to the front sleeve such that a ratio of the a cross-sectional area of the bypass taken along a plane orthogonal to the axial direction of the cartridge at the other end of the bypass to that taken along a plane orthogonal to the axial direction of the cartridge at the one end of the bypass ranges from 1.2 to 5.0.

* * * * *